United States Patent [19]

Bark

[11] Patent Number: 4,533,349
[45] Date of Patent: Aug. 6, 1985

[54] SKIN MOUNTED DRAINAGE CATHETER RETENTION DISC

[75] Inventor: Jeffrey E. Bark, Tulsa, Okla.

[73] Assignee: Medical Engineering Corporation, Racine, Wis.

[21] Appl. No.: 439,739

[22] Filed: Nov. 8, 1982

[51] Int. Cl.$^3$ ............................................. A61M 25/02
[52] U.S. Cl. .............................. 604/174; 128/DIG. 26; 604/180
[58] Field of Search .................. 604/174, 179, 180; 128/133, DIG. 26

[56] References Cited

U.S. PATENT DOCUMENTS

| 3,176,690 | 4/1965 | H'Doubler | 128/DIG. 26 |
| 3,568,679 | 3/1971 | Reif | 604/180 |
| 4,080,970 | 3/1978 | Miller | 604/174 |
| 4,397,641 | 8/1983 | Jacobs | 604/180 |
| 4,419,094 | 12/1983 | Patel | 604/180 |
| 4,435,174 | 3/1984 | Redmond et al. | 604/174 |

*Primary Examiner*—Dalton L. Truluck
*Attorney, Agent, or Firm*—Quarles & Brady

[57] ABSTRACT

A skin mounted retention disc for maintaining a catheter indwelling comprises an elastomeric disc having a centrally disposed bore therethrough dimensioned to receive the catheter. About the periphery of the elastomeric disc is a plurality of very small holes to enable the disc to be sutered to the skin. Integrated to and extending upwardly from the elastomeric disc is a projection having a helically disposed channel therein for engaging the catheter as the catheter tube is wrapped about the disc after exiting the skin. A connecting tube having low release force connectors at either end is secured to the disc and links the catheter to a drainage bag. Because the force required to break the connection between the connecting tube and either the drainage bag or the catheter is less than the force required to dislodge the skin mounted retention disc, the connecting tube serves as a safety release to prevent the disc from becoming dislodged should the patient stray from the drainage bag.

5 Claims, 5 Drawing Figures

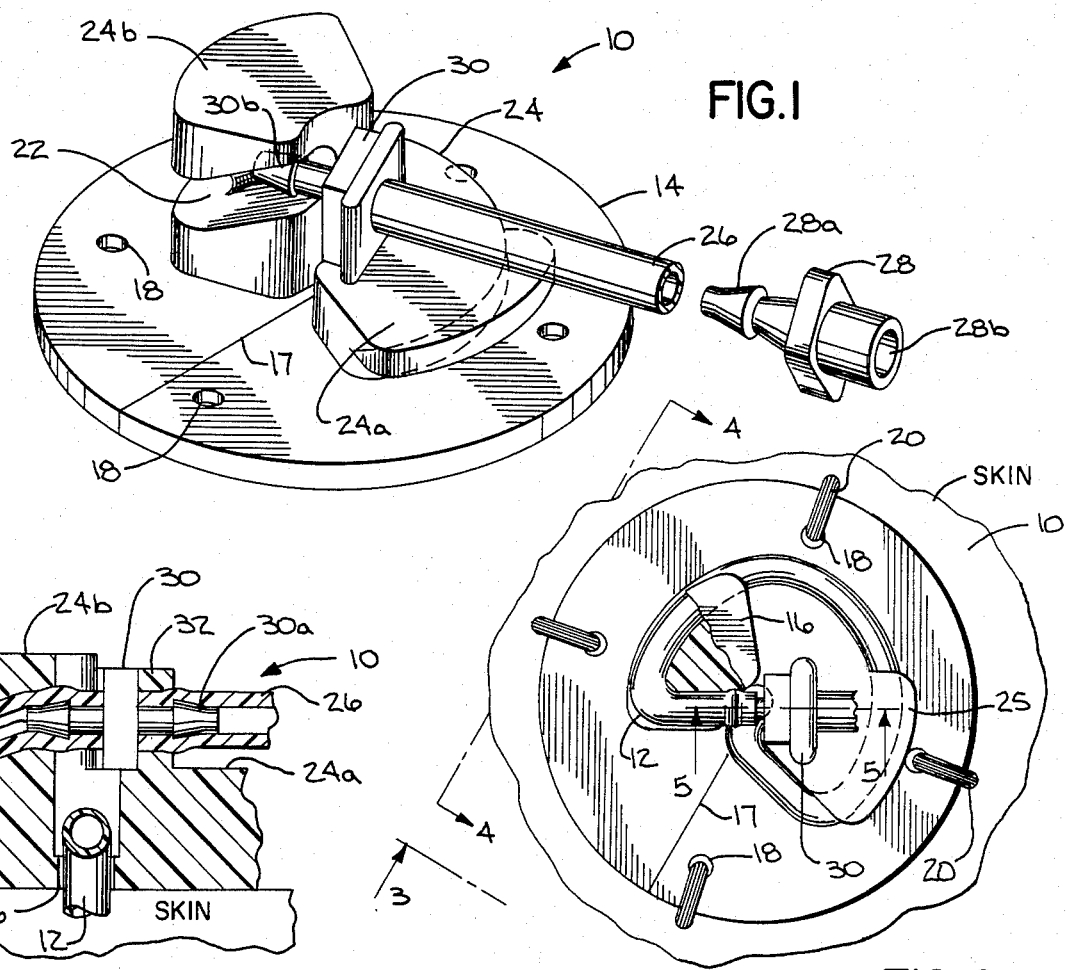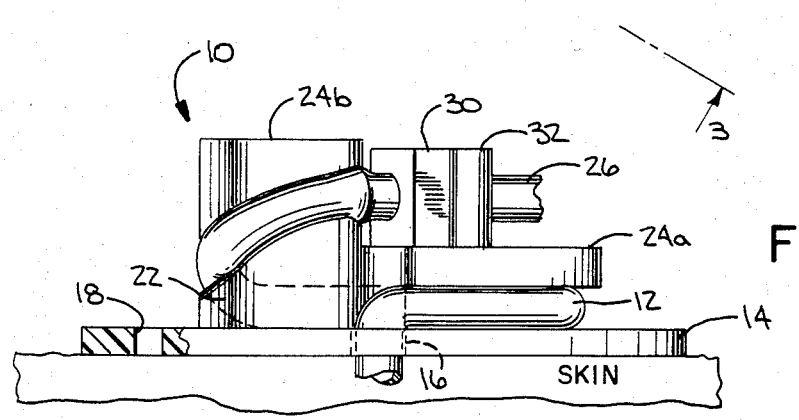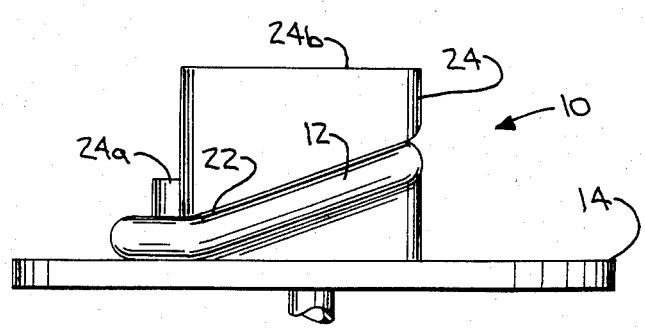

SKIN MOUNTED DRAINAGE CATHETER RETENTION DISC

FIELD OF THE INVENTION

This invention relates generally to skin mounted retention discs for retaining a drainage catheter indwelling within a patient.

BACKGROUND OF THE INVENTION

Certain surgical procedures such as a subcutaneous nephrostomy (kidney drainage) require that a drainage catheter remain in the patient for an extended period of time. To maintain the catheter indwelling, a skin mounted retention disc, such as are known in the art, is commonly employed. A typical, prior art retention disc has a centrally extending bore so that the drainage catheter may be inserted therethrough and into the skin. Usually, a tie or other mechanical fastener is provided to secure the catheter to the disc. The disc itself is typically secured to the patient by sutures or by an adhesive.

The above described prior art retention disc is believed to be subject to the following disadvantages. Firstly, and most importantly, if a patient, especially a delirious patient, who has a skin mounted retention disc secured to his or her skin either by sutures or adhesives, attempts to separate himself or herself from the drainage bag, it is likely that the skin mounted retention disc will be pulled from the skin before the catheter is dislodged from the drainage bag. Once the skin disc has been pulled from the skin, the skin mounted retention disc must be reattached by the patient's doctor. Secondly, with prior art skin mounted retention discs, separate mechanical fasteners, such as a pull tie, are usually required to secure the catheter directly to the retention disc. The need for a separate fastener to secure the drainage catheter to the retention disc increases the time and effort required to install the catheter and disc.

In contrast, the present invention concerns an improved, skin mounted drainage catheter retention disc which advantageously secures a drainage catheter thereto without the need for separate mechanical fasteners.

It is an object of the present invention to provide an improved skin mounted drainage catheter retention disc;

It is yet another object of the present invention to provide improved skin mounted drainage catheter retention discs for retaining a drainage catheter indwelling without the need for separate mechanical fasteners;

It is yet another object of the present invention to provide an improved skin mounted drainage catheter retention disc which enables the drainage catheter to be advantageously disconnected from its drainage bag upon separation of the catheter from the drainage bag without disturbing the mounting of the retention disc to the skin.

BRIEF SUMMARY OF THE INVENTION

Briefly, in accordance with the preferred embodiment of the invention, an improved skin mounted retention disc for retaining a drainage catheter indwelling comprises a disc configured of an elastomeric material such as silicone rubber or the like. Centrally disposed through the disc is a passageway which is dimensioned to receive the drainage catheter so that the drainage catheter extends through the disc and into the skin. Located on the disc is a catheter guide which takes the form of a radiused channel helically disposed in a raised portion of the disc adjacent to the bore through the disc. The radiused channel is dimensioned to receive the drainage catheter as it extends up from the disc so that the drainage catheter can be made fast to the disc by wrapping the catheter about the disc, thereby eliminating the need for separate mechanical fasteners. To prevent the catheter from becoming dislodged when the patient inadvertently separates himself or herself from the drainage bag, a connecting tube is attached to the skin disc and has at least one low release force connector at either end thereof for engaging the free end of either of the catheter and the catether drainage bag, respectively. In this way, if a patient having the skin mounted retention disc secured thereto attempts to separate himself or herself from the drainage bag, then the connection between the drainage bag and connecting tube is broken before the skin mounted retention disc is separated from the patient.

BRIEF DESCRIPTION OF THE DRAWINGS

The features of the invention believe to be novel are set forth with particularity in the appended claims. The invention itself, however, both as to organization and method of operation, together with further objects and advantages thereof may be best understood by reference to the following description taken in conjunction with the accompanying drawings in which:

FIG. 1 is a perspective view of the skin mounted retention disc of the present invention with the connecting tube attached;

FIG. 2 is a top view of the skin mounted retention disc of FIG. 1 with the catheter attached and the disc sutured to the patient's skin;

FIG. 3 is an end view of the skin mounted retention disc of FIG. 2 taken along lines 3—3 thereof;

FIG. 4 is an end view of the skin mounted retention disc of FIG. 2 taken along lines 4—4 thereof; and FIG. 5 is a cross-sectional view of the skin mounted retention disc of FIG. 1 taken along lines 5—5 of FIG. 2.

DETAILING DESCRIPTION OF THE PREFERRED EMBODIMENT

Referring now to the drawings, FIGS. 1-5 illustrate differing views of a skin mounted retention disc 10 for retaining a drainage catheter, such as drainage catheter 12 as illustrated in FIGS. 2, 3 and 4, indwelling in a patient for draining a kidney or other organ. Disc 10 is configured of a thin pad 14 of elastomeric material, such as silicone rubber or latex rubber or polyvinylchloride. While the pad 14 could be made from other materials, configuring the pad of an elastomeric material imparts pliability to the pad which is generally desirable. Centrally disposed through pad 14 is a passageway 16 (FIGS. 3 and 5) which is dimensional to receive drainage catheter 12 so that the catheter can extend through the disc and into the skin. A radial slit 17 (FIGS. 1 and 2) in pad 14 facilitates insertion of the drainage catheter into passageway 16. In addition to having a centrally disposed passageway 16, pad 14 is also provided with a plurality of passageways 18 spaced about the periphery of the pad. As best illustrated in FIG. 2, passageways 18 accommodate sutures 20 to enable the pad to be sutured to the skin without the need to cut the pad and thereby risk pad tearing.

To retain catheter 12, the skin disc 10 of the present invention has a radiused channel 22 thereon dimensioned to receive and engage the catheter. In the presently preferred embodiment, radiused channel 22 is helically disposed in a kidney shaped projection 24 integrated to, and extending upwardly from pad 14. Projection 24 has a lower and upper parallel surfaces 24a and 24b, respectively, the lower parallel surface 24a having an overhanging edge 25. Once the catheter 12 is disposed through pad 14 and into the skin, the upwardly extending portion of the catheter is wrapped underneath edge 25 as illustrated in FIGS. 2 and 3 and is pressed into the radiused channel 22 so that the catheter is firmly secured to the skin retention disc 10 without the need for any mechanical fasteners. Not only does the skin mounted retention disc 10 retain the catheter without need for external fasteners, but skin mounted retention disc 10 easily allows the catheter position to be changed by simply unwrapping the catheter, and then repositioning it as required before re-wrapping the catheter to disc 10. Moreover, by keeping the catheter close to the skin, the skin mounted retention disc 10 aids in patient comfort.

An important aspect of the skin mounted retention disc 10 of the present invention is the ability of disc 10 to retain catheter 12 even if the disc and catheter are displaced from the drainage bag (not shown) associated with the catheter as may occur if a delirious patient walks away from his or her drainage bag. To this end, a connecting tube 26 is provided for connecting drainage catheter 12 to its associated drainage bag. Connecting tube 26 has its end distal from pad 14 mated with the male barb 28a at one end of a low release force connector 28. The connector 28 has a female luer 28b at its opposite end for attachment to a drainage bag (not shown). Connecting tube 26 has its end proximate to disc 10 mated to the male barb 30a at one end of low release force connector 30. The barb 30a of connector 30 is of sufficient length to first pass through the bore in a post 32 extending upwardly from surface 24a of projection 24 before the barb mates with connecting tube 26. In this way the connecting tube is secured to the skin mounted retention disc. The male barb 30b on the other end of connector 30 mates with the distal end of catheter 12.

Connecting tube 26 and connectors 28 and 30 serve in combination as a safety release for the skin mounted retention disc. With connectors selected so that the male barb on one of the connectors is slightly undersized, a force of approximately 6 to 7 pounds is required to break the connection between either of connectors 28 and 30 and connecting tube 26. However, a force of 10 or more pounds is usually required to dislodge the skin retention disc. Thus, the connection between connecting tube 26 one of connectors 28 and 30 breaks with a much lower force than the amount of force required to dislodge the skin mounted retention disc, assuring that the connection between the drainage bag and the catheter will break before the skin mounted retention disc becomes dislodged.

The skin mounted retention of the present invention can easily and cheaply be manufactured because pad 14 with its radiused channel 22 disposed in projection 24 can be molded as a single unitary structure. Installation of skin mounted retention disc is also made easy by virtue of lack of any need for separate fasteners to secure the catheter. Further, the pre-cut suture holes eliminate the need to cut and possibly tear the disc.

The foregoing discloses an improved skin mounted retention disc for retaining a catheter indwelling.

While only certain preferred features of the invention have been shown by way of illustration, many modifications and changes will occur to those skilled in the art. It is, therefore, to be understood that the appended claimed are intended to cover all such modifications and changes as found in the true spirit of the invention.

What is claimed is:

1. An improved skin mounted retention disc for retaining a drainage catheter indwelling comprising:
   a substrate having a bore disposed therethrough dimensioned to receive a drainage catheter so that the catheter can be inserted through the disc and into the skin;
   guide means integrated to said disc for engaging the drainage catheter to retain the drainage catheter to said disc; and
   safety release connecting means for connecting the drainage catheter to a drainage bag and for breaking the connection between the drainage catheter and the drainage bag once said disc is displaced from the drainage bag, thereby avoiding separation of said skin mounted retention disc from the patient's skin.

2. The invention according to claim 1 wherein said guide means comprises a raised portion extending upwardly from said disc, said raised portion having a radiused channel therein dimensioned to receive the drainage catheter.

3. The invention according to claim 1 wherein said safety release connecting means comprises:
   a first low release force connector attached to said projection, said first connector having a first barb at one end thereof for mating with the drainage catheter and having a second barb at the opposite connector end;
   a connecting tube having one end thereof attached to said second barb of said first connector; and
   a second connector having a barb at one end thereof for mating with the other of the ends of said connecting tube and said second connector having a luer at its opposite end for mating with a drainage bag.

4. An improved skin mounted retention disc for retaining a drainage catheter indwelling comprising:
   a disc having a centrally disposed bore therethrough dimensioned to receive a drainage catheter to enable the catheter to be inserted through the disc and into the skin;
   guide means integrated to said disc, said guide means dimensioned for engaging the catheter to retain the catheter to said disc and comprising a raised portion integrated to and extending upwardly from said disc, said raised portion having a helically disposed radiused channel therein for receiving the drainage catheter; and
   an overhanging edge on said raised portion lying substantially along the path of curvature of said helically disposed radiused channel for retaining the drainage catheter when the drainage catheter is wrapped around said raised portion so as to be seated within said helically disposed channel.

5. An improved skin mounted retention disc for retaining a catheter indwelling comprising:
   a substrate having a centrally disposed bore for receiving the drainage catheter;

a raised portion integrated to and extending upwardly from said substrate adjacent to said substrate bore, said raised portion having a helically disposed radiused channel therein dimensioned to receive a drainage catheter when the drainage catheter is wrapped about said raised portion upon exiting said substrate bore; and a pair of horizontally oriented parallel surfaces, one of said pair of parallel surfaces having an overhanging edge lying substantially within the path of curvature of said helically disposed channel for retaining the drainage catheter as the catheter leaves said radiused channel.

* * * * *